United States Patent
Waterbury et al.

(12) 
(10) Patent No.: US 6,255,353 B1
(45) Date of Patent: Jul. 3, 2001

(54) INHIBITION OF ANGIOGENESIS

(75) Inventors: Lowell D. Waterbury, San Carlos; Kenneth W. Narducy, San Jose; Allan L. Wilcox, Mountain View, all of CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/267,510

(22) Filed: Mar. 12, 1999

Related U.S. Application Data
(60) Provisional application No. 60/077,876, filed on Mar. 13, 1998.

(51) Int. Cl.⁷ .................................................. A61K 31/255
(52) U.S. Cl. .......................... 514/643; 514/517; 514/518; 514/645; 562/30; 562/66; 564/253; 564/282; 564/284
(58) Field of Search .................................. 562/57, 30, 66; 564/253, 284, 282; 514/517, 518, 643, 645

(56) References Cited

FOREIGN PATENT DOCUMENTS

WO 95/17876 * 7/1995 (WO).
WO 97/39751 * 10/1997 (WO).

* cited by examiner

*Primary Examiner*—Paul J. Killos
(74) *Attorney, Agent, or Firm*—Burns, Doane, Swecker & Mathis, LLP

(57) ABSTRACT

Certain simple chemical agents, referred to herein as nitrone related therapeutics or "NRTs", when administered to a patient susceptible to neovascularization (angiogenesis), can intervene and inhibit the disease's progress. Methods for therapeutically and prophylactically inhibiting angiogenesis by administering one or more NRTs are disclosed as are pharmaceutical compositions for use in such methods of treating. NRTs useful in these compositions and therapeutic methods are also disclosed.

25 Claims, 7 Drawing Sheets

INHIBITION OF ANGIOGENESIS

This application claims benefit of provisional application 60/077,876, filed Mar. 13, 1998.

BACKGROUND OF THE INVENTION

1. Field of the Invention

The invention relates to compounds, compositions and methods for inhibiting (preventing and treating) neovascularization (angiogenesis).

2. Prior Work

Malignant neovascularization (angiogenesis), particularly ocular neovascularization associated with macular degeneration, diabetic retinopathy and retinopathy of prematurity, as well as psoriasis, rheumatoid arthritis and solid tumors, is a serious medical condition.

The most common cause of blindness in Americans over age 55 is age-related macular degeneration (AMD); for those under 40, diabetes is the most common cause of blindness. Neovascularization is the root cause of blindness in both cases. Neovascularization is the result of a compromise of the vascular bed supplying the retina, and may be regarded as a response to tissue ischemia (or hypoxia). Clinicians have long recognized the high probability of neovascularization in individuals who have lost part of the capillary bed due to diabetes, or who have experienced occlusion of a branch vein of the retina.

The primary current treatment for neovascularization is destructive. Photocoagulation is used to reduce the volume of hypoxic tissue in diabetic retinopathy or to destroy vessels in AMD. Cryotherapy may be used to destroy hypoxic retina in infants. There is an urgent need for therapeutic intervention in these disease processes. No known therapeutic treatment can prevent neovascularization following loss of capillaries in diabetes, reduce the risk of further neovascularization in wet AMD, or offer reassurance to patients at risk because of heredity, diabetes, or age.

Any progress toward therapeutic management and prevention of neovascularization will greatly reduce the social and economic impact of diabetes and AMD.

One of the limitations of the newer therapeutic approaches to neovascularization that are under development, particularly those involving growth factors, is that they may also inhibit wound repair or the development of collateral vessels in mild occlusion of coronary arteries.

STATEMENT OF THE INVENTION

It has now been found that certain simple chemical agents, referred to herein as nitrone-related therapeutics or "NRTs", when administered to a patient susceptible to angiogenesis, can intervene and inhibit its progress.

In one aspect this invention provides a method for inhibiting angiogenesis in a patient susceptible thereto by administering to that patient an effective angiogenesis-inhibiting dose of one or more NRTs.

In a second aspect, this invention provides pharmaceutical compositions for use in such methods of treating. These compositions include one or more NRTs in a pharmaceutically acceptable carrier.

In a third aspect, this invention provides NRTs useful in these compositions and therapeutic methods.

DETAILED DESCRIPTION OF THE INVENTION

Brief Description of the Drawings

This invention will be further described with reference being made to the accompanying drawings in which.

DESCRIPTION OF PREFERRED EMBODIMENTS

Figure 1:
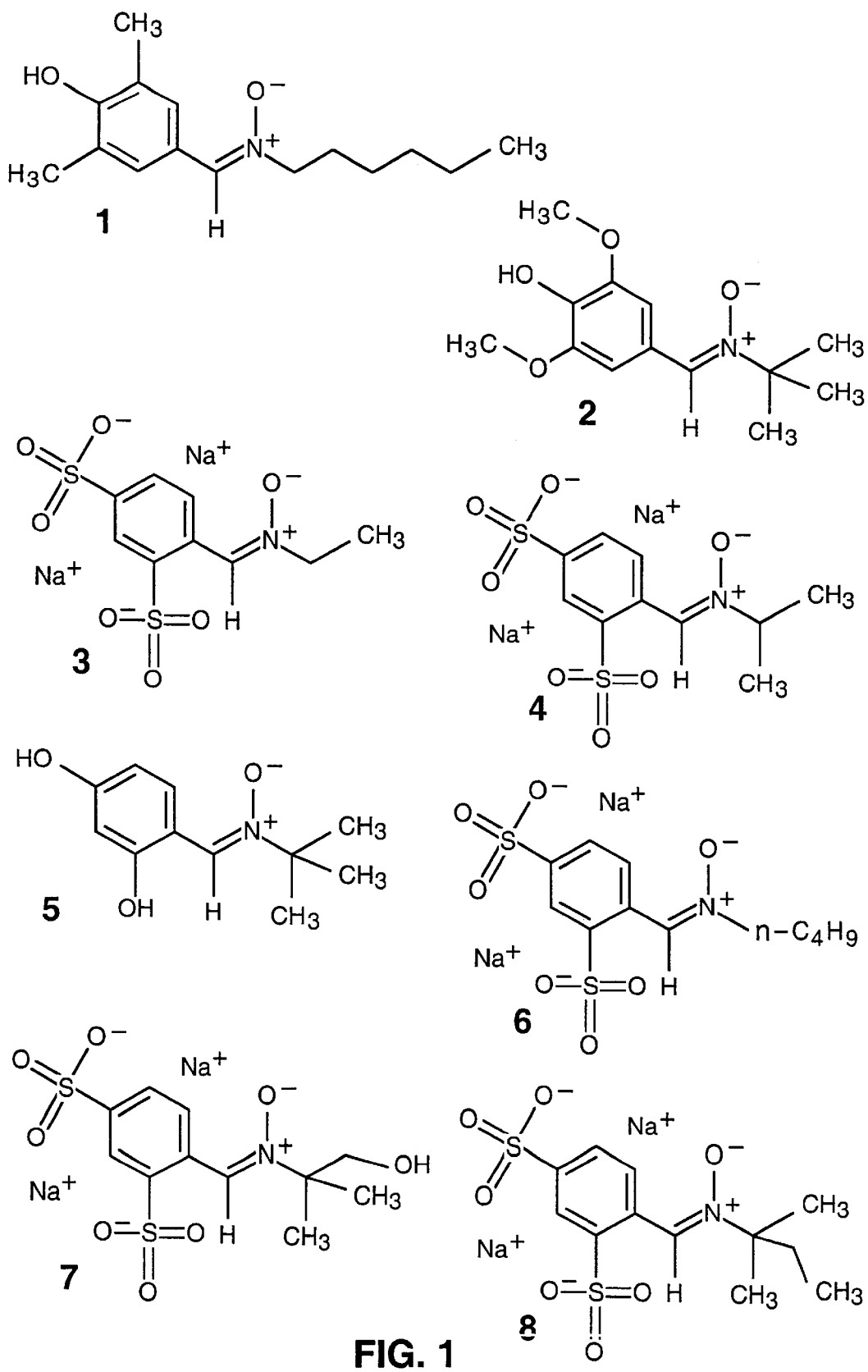
FIG. 1 is a depiction of the chemical structures of ten NRTs preferred for use in the practice of the invention.

This Description of Preferred Embodiments is broken into the following segments:

The NRTs

Pharmaceutical Preparations, Modes of Administration and Dosages

Methods of Preparation of NRTs

Description of Experiments

The NRTs

The NRTs which are employed in the practice of this invention are generally classed as spin-trapping agents. They include aromatic nitrones, including the best known nitrone, alpha-phenyl-N-t butyl nitrone ("PBN") and derivatives thereof; pyrolline N-oxides such as 5,5-dimethyl pyrroline N-oxide ("DMPO") and derivatives thereof; pyridyl N-oxide nitrones such as alpha-(4-pyridyl-1-oxide)-N-butyl nitrone ("POBN") and derivatives thereof. Examples of useful materials are described in U.S. Pat. No. 5,622,994 and published PCT application number WO 92/22290, both of which are incorporated herein by reference.

Among the NRT materials, aromatic nitrones are preferred. Aromatic nitrones are generally depicted by the formula

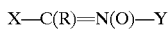

wherein X is an aromatic group, particularly a phenyl group or a phenyl group with at least one and particularly up to about three substituents selected from the following:

lower alkyls of from one to about four carbon atoms, which may be linear or branched, and particularly methyls;

lower alkenyls; halogens; haloalkyls; hydroxys; primary, secondary and tertiary amines; NOs; amides;

lower alkoxyls, of from one to about four carbon atoms and particularly methoxyls;

carboxylic acid functionalities, present as free acid —COOH groups or as suitable salts or esters such as lower alkyl esters of from one to about four carbon atoms and particularly methyl esters;

sulfur-containing acid functionalities such as sulfates, sulfites and sulfonates, with the sulfates and sulfites being present as free acids or as salts.

In this formula R is most typically hydrogen but can also be a lower alkyl, lower alkoxyl or the like, wherein "lower" has the one to four carbon atom meaning set forth above.

In this formula Y is most commonly a one to twelve carbon alkyl group which may be straight chain or branched chain and which may be unsubstituted hydrocarbyl or may contain one or more heteroatoms substituents such as oxygen, sulfur, nitrogen or the like. These heteroatoms can be present as substituents in the Y group's main structural chain, for example as ether oxygens. Alternatively, the heteroatoms can be in the form of groups depending from the Y group main chain. Most commonly Y is from about two to about eight carbon atoms in size with no or one hydroxy or alkoxy substituents. Representative Y groups include methyl; ethyl; the propyls including n- and i-propyl; the butyls, especially t-butyl, heteroatom-substituted (such as hydroxy-substituted-) t-butyl and n-butyl; pentyls such as 1,1-dimethyl propyl and n-pentyl; the hexyls, heptyls and octyls.

Some of these compounds include sulfate, sulfone, sulfoxide, sulfonamide or carboxylate groups. The sulfate groups can be present in an at least partially protonated acid form as a solid and in solution at low pH conditions. The weaker acid groups, such as carboxylates, are present as acids at somewhat higher pH's. These ionizable acid groups can also exist at higher pHs in an ionized salt form in combination with pharmaceutically acceptable cations. Most commonly, these cations are a monovalent material such as sodium, potassium or ammonium, but can also be a multivalent cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. When reference is made herein to these sulfate or carboxylate groups or the like it will be understood to include the acid form as well as these salt forms, unless otherwise expressly stated. Often the salt forms are more stable than the corresponding free acids.

Among these acid groups, the simple sodium, potassium and ammonium salts are most preferred with the calcium and magnesium salts also being preferred but somewhat less so.

In the case of the other general types of NRTs, such as those based upon POBN or DMPO, the same types of substitutions can be employed as described with reference to the PBN type nitrones.

Thus, in summary, the NRTs preferably used in this invention can be selected form the groups of aromatic nitrones of the formula X—C(R)═N(O)—Y, wherein X, R and Y are defined above;

PBN derivatives of the formula X—C(R)═N(O)—Y, wherein X is a phenyl or a phenyl with substituents, and R and Y are defined above;

DMPO and derivatives thereof of the general formula

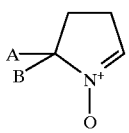

wherein A and B are each methyls or are each of the substituents listed with reference to the general aromatic nitrone formula; and POBN and derivatives thereof of the general formula

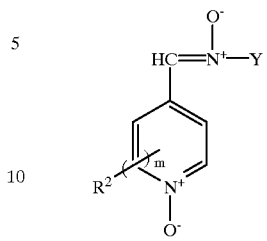

wherein Y is as defined above, n is 0 to 4 and $R^2$ is any of the substituents listed with reference to the aromatic nitrones.

A group of most preferred NRTs is depicted in FIG. 1. These materials include the following compounds which are at times described using the noted compound references:

(Compound Number 1) 3,5-dimethyl,4-hydroxyphenyl-N-n hexyl nitrone;

(Compound Number 2) 3,5-dimethoxy,4-hydroxyphenyl-N-t butyl nitrone;

(Compound Number 3) 2,4-disulfophenyl-N-ethyl nitrone, disodium salt;

(Compound Number 4) 2,4-disulfophenyl-N-isopropyl nitrone, disodium salt;

(Compound Number 5) 2,4-dihydroxyphenyl-N-t butyl nitrone;

(Compound Number 6) 2,4-disulfophenyl-N-n butyl nitrone, disodium salt;

(Compound Number 7) 2,4-disulfophenyl-N-1,1-dimethyl, 2-hydroxyethyl nitrone, di-sodium salt; and (Compound Number 8) 2,4-disulfophenyl-N-t amyl nitrone, disodium salt.

Of these, 3,5-dimethyl,4-hydroxyphenyl-N-n hexyl nitrone is the most preferred at this time.

Pharmaceutical Preparations, Modes of Administration and Dosages

Pharmaceutical preparations based upon the NRTs include one or more NRT in combination with a pharmaceutically acceptable carrier. The particular carrier employed will depend upon the mode of administration. Our studies provide evidence that the NRTs are effective in the treatment of angiogenesis when administered systemically, such as parenterally or orally. We also have evidence that the NRTs are active against angiogenesis when administered locally such as by intravitreal injection to the eye or topically to the eye via ointments, via eye drops of solutions or suspensions of particles or of liposomes or from a drug-releasing ocular insert.

The compositions for oral administration can take the form of bulk liquid solutions or suspensions or bulk powders. More commonly, however, the compositions are presented in a unit dosage form to facilitate accurate dosing. Typical unit dosage forms include prefilled, premeasured ampules or syringes of the liquid compositions or pills, tablets, capsules or the like in the case of solid compositions. In such compositions, the NRT is usually a minor component (0.1 to say 50% by weight or preferably from about 1 to about 40% by weight) with the remainder being various vehicles or carriers and processing aids helpful for forming the desired dosing form. A liquid form may include a suitable aqueous or nonaqueous vehicle with buffers, suspending and dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In the case of injectable compositions, they are commonly based upon injectable sterile saline or phosphate-buffered saline or other injectable carriers (both aqueous and nonaqueous) known in the art. Again the active NRT is typically a minor component, often being from about 0.05 to 10% by weight with the remainder being the injectable carrier and the like.

These components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated by reference.

When treating ocular neovascularization conditions, one can also administer the compounds of the invention topically to the eye in the form of an ocularly acceptable eye drop or suspension of particles or liposomes, from ointments or from a suitable sustained release form. Eye drops include a liquid carrier which is typically isotonic and sterile and also includes a suitable preservative and thixotropic material. Representative topical ocular preparations are described in chapter 2 "Pharmacokinetics: Routes of Administration", pages 18–43, of *Ocular Pharmacology*, Fifth Edition, William Havener, The C. V. Mosby Company, St. Louis, 1983, which is also incorporated herein by reference. As pointed out there, eye drop formulations may be based on simple aqueous vehicles or may employ more viscous vehicles such as thickened aqueous vehicles or nonaqueous materials such as vegetable oils or the like all with various buffers and salts to adjust the pH and tonicity to non-irritating levels. In these eye drop formulations the NRT can be present as a solute or as a suspension or in the form of liposomes based on phospholipids and the like.

Ocular ointments include a gel or ointment base as described in Havener's *Ocular Pharmacology*. In these topical compositions the amount of NRT will range from about 0.05 to 10% by weight with the remainder being the carrier and the like. Typical concentrations for eye drops are 0.25–2% by weight.

When direct delivery of NRT to the eye is desired, it may also be accomplished using sustained release forms or sustained release drug delivery systems. A description of representative sustained release materials such as soft contact lenses, soluble drug inserts and membrane-controlled diffusional systems, can be found in the incorporated materials in Havener's *Ocular Pharmacology*.

The conditions treated with the NRT-containing pharmaceutical compositions may be classed generally as malignant neovascularization (angiogenesis) conditions. These occur with particular severity as ocular neovascularization associated with macular degeneration, diabetic retinopathy and retinopathy of prematurity. Angiogenesis is also observed in psoriasis, rheumatoid arthritis, and solid tumors. Each of these conditions is characterized by a progressive loss of function, such as vision, range of motion or skin integrity. The NRT compounds, when administered orally or by injection such as intravenously, can slow and delay and possibly even to some extent reverse the loss of function.

Injection dose levels such as by intravenous administration for treating these conditions range from about 0.01 mg/kg/hr to about 10 mg/kg/hour. Such intravenous therapy might last for from less than a hour to as long as eight hours or more. A preloading bolus of from about 0.1 mg/kg to about 10 mg/kg or more may also be administered to achieve adequate steady state levels. The maximum total dose is not expected to exceed about 2 g/day for a 40 to 80 kg adult patient.

Many of the conditions treated are chronic in nature. With these chronic conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose commonly provides from about 1 to about 20 mg/kg of NRT, with preferred doses each providing from about 1 to about 10 mg/kg and especially about 1 to about 5 mg/kg.

In the case of treating angiogenesis associated with solid tumors, one can of course use systemic administration as just described. One can also use more localized delivery to the tumor site. This can be accomplished by close intra-arterial delivery where the artery chosen is one delivering blood to the tumor site where the angiogenesis is occurring. In the case of close intra-arterial administration one typically administers doses of up to about 10 mls, e.g. from about 0.25 to about 10 mls, containing from about 0.1 to about 10 and preferably from about 0.5 to about 5 mg/ml of active NRT. In the case of treating angiogenesis associated with solid tumors, the doses of NRT can be delivered daily or more often during the therapy period. One could also administer the active NRT by a continuous pumping into the arterial delivery route or continuously from a depot or other site within or near the tumor.

Of course, one can administer an NRT as the sole active agent or one can administer it in combination with other agents, including other active NRTs.

Methods of Preparation of NRTs

Many of the NRTs employed herein are known compounds which may be purchased or which may be prepared by methods described in the literature. In addition, in the case of the NRTs which are simple nitrones, such as the PBN analogues described above as most preferred materials, these materials can be produced using a two step synthesis.

In the first step, a commercially available nitroalkane (wherein the alkane corresponds to the R group present on the nitrogen in the final nitrone functionality) (for example 2-nitropropane or 2-nitrobutane) is converted to the corresponding hydroxylamine using a suitable reagent such as activated zinc/acetic acid, activated zinc/ammonium chloride or an aluminum/mercury amalgam. This reaction can be carried out in 0.5 to 12 hours and especially about 2 to 6 hours or so at a temperature of about 0 to 100° C. in a liquid reaction medium such as alcohol/water mixture in the case of the zinc reagents or an ether/water mixture in the case of the aluminum amalgam reactant.

In the second step, the freshly formed hydroxylamine is reacted in slight molar excess with a formyl-substituted aromatic compound which corresponds to the aromatic portion of the desired NRT. If the aromatic portion carries an acid substituent such as sulfonic acid or carboxylic acid functionality, this group will be present in the salt form. The position of the formyl group corresponds to the position of the nitrone in the final product, for example 2,4-dihydroxy benzaldehyde. The number (0, 1, 2 or 3) and position (2, 3, 4, 5, or 6) of the substituents on the aromatic ring corresponds to the number and position in the final product. This reaction can be carried out at similar temperature conditions described with reference to the first step. This reaction is generally complete in 1 to 48 hours and especially 10 to 24 hours.

If the product so formed contains a sulfate, carboxylate or the like, such group is typically present as the salt. These salts can be converted to the free acid form by suitable acidification. Other salts can be easily formed by admixing the free acid in aqueous medium with the appropriate base, for example, KOH for the potassium salt, and the like.

Description of Examples

This invention will be further described with reference being made to the following experiments. These are intended to exemplify preferred aspects of this invention and are not to be construed as limiting its scope.

Two in vitro experiments were conducted as Example 1 and 2 to determine whether or not NRTs showed promise as active agents against neovascularization.

EXAMPLE 1

Figure 2:
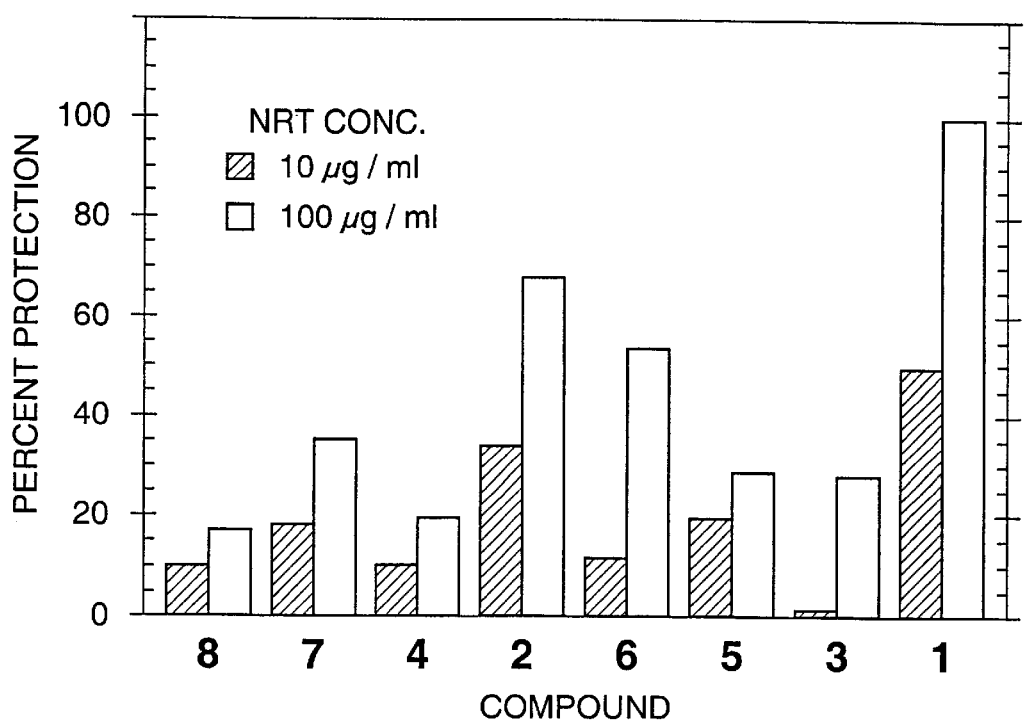
FIG. 2 is a series of bar graphs illustrating the effect of NRTs in preventing lipid peroxidation in bovine retinal homogenates.

In the first test, selected NRTs were tested for their ability to prevent lipid peroxidation of bovine retinal homogenates. Lipid peroxidation was induced by the addition of 2.5 mM $Fe^{+2}$. NRTs were added to give concentrations of 10 and 100 μg/ml which is approximately 40–400 μM depending on the molecular weight of the NRT tested. Lipid peroxidation was measured by a TBARs assay. This assay is based on a modification of a fluorescent method reported by Yagi (Biochem. Med. 25:373–378(1981)). Of the eight NRTs tested, all were active as shown in FIG. 2 and in Table 1.

EXAMPLE 2

Figure 3:
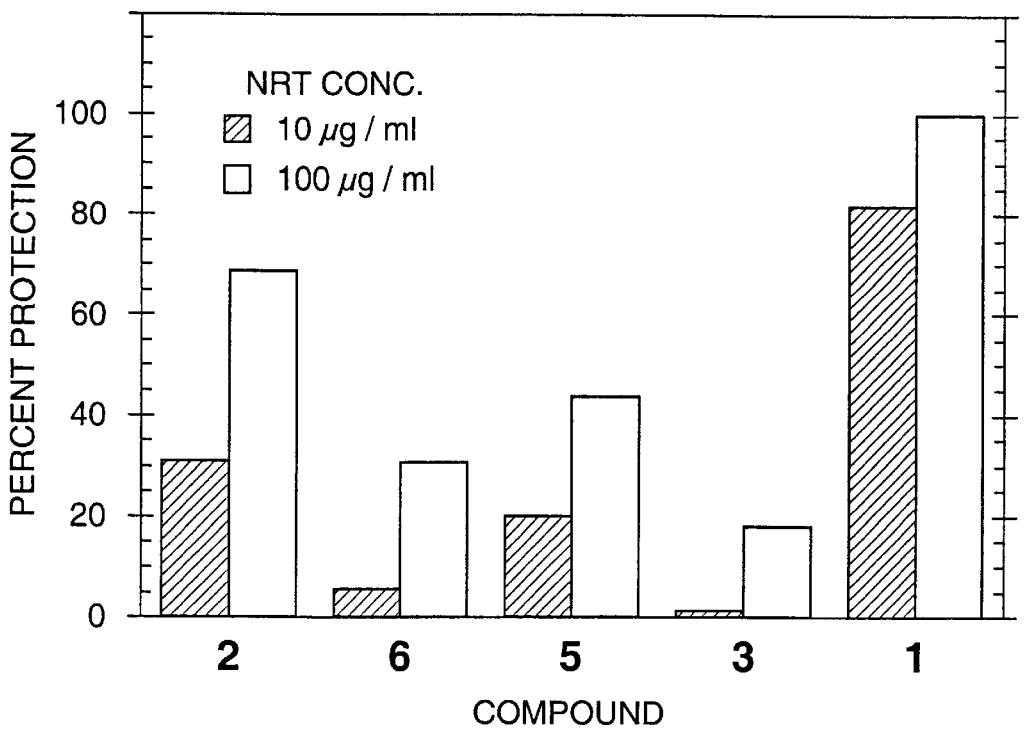
FIG. 3 is a series of bar graphs illustrating the effect of NRTs in preventing lipid peroxidation in isolated bovine retinal pigment epithelium cells.

In the second test, selected NRTs were tested to determine their effect on preventing lipid peroxidation of isolated bovine retinal pigment epithelium cells. Lipid peroxidation was induced by the addition of 2.5 mM $Fe^{+2}$. NRTs were added to give concentrations of 10 and 100 μg/ml which is approximately 40–400 μM depending on the molecular weight of the NRT tested. Lipid peroxidation was measured by a TBARs assay. This assay is based on a modification of a fluorescent method reported by Yagi (Biochem. Med. 25:373–378(1981)). Of the eight NRTs tested, five were active as shown in FIG. 3 and in Table 1.

TABLE 1

Activity of NRTs in In Vitro Assays
Testing Ability to Inhibit Lipid Peroxidation

| Bovine Retinal Homogenate | | | Isolated Bovine Pigment Epithelium | | |
|---|---|---|---|---|---|
| Compound | Concentration | Inhibition | Compound | Concentration | Inhibition |
| 1 | 10 μg/ml | 49% | 1 | 10 μg/ml | 82% |
| | 100 μg/ml | 100% | | 100 μg/ml | 31% |
| 2 | 10 μg/ml | 33% | 2 | 10 μg/ml | 31% |
| | 100 μg/ml | 67% | | 100 μg/ml | 69% |
| 6 | 10 μg/ml | 11% | 5 | 10 μg/ml | 19% |
| | 100 μg/ml | 53% | | 100 μg/ml | 44% |
| 7 | 10 μg/ml | 18% | 6 | 10 μg/ml | 5% |
| | 100 μg/ml | 35% | | 100 μg/ml | 30% |
| 5 | 10 μg/ml | 19% | 3 | 10 μg/ml | 0% |
| | 100 μg/ml | 28% | | 100 μg/ml | 18% |
| 4 | 10 μg/ml | 10% | 7 | 10 μg/ml | 0% |
| | 100 μg/ml | 19% | | 100 μg/ml | 0% |

TABLE 1-continued

Activity of NRTs in In Vitro Assays
Testing Ability to Inhibit Lipid Peroxidation

| Bovine Retinal Homogenate | | | Isolated Bovine Pigment Epithelium | | |
|---|---|---|---|---|---|
| Compound | Concentration | Inhibition | Compound | Concentration | Inhibition |
| 8 | 10 μg/ml | 10% | 8 | 10 μg/ml | 0% |
| | 100 μg/ml | 17% | | 100 μg/ml | 0% |
| 3 | 10 μg/ml | 0% | 4 | 10 μg/ml | 0% |
| | 100 μg/ml | 27% | | 100 μg/ml | 0% |

EXAMPLE 3

In one animal model for neovascularization, New Zealand white rabbits were treated with lipid hydroperoxide ("LHP"). In comparison to animals not so treated or treated with non-hydroperoxidized lipid (18:1 linoleic acid), these animals develop high degrees of neovascularization in their corneas and retina. A test material's effectiveness is measured by its ability to intervene in the neovascularization event.

In one study, neovascularization of the cornea was examined. Vessels in the superior quadrant which were stimulated by LHP served as the positive control. They grew progressively to a mean length of 2.4 mm. There were approximately 20 separate vessels arising from the parent limbal vessels. Multiple branches were observed in this quadrant especially at the distal ends. Vessels in the center were always longer than at the edges. This was because neovascularization is a function of distance between the stimulus and the limbus. Thus, vessels were never observed in the inferior or intermediate quadrants. The controls using non-peroxidized linoleic acid (18:1) were essentially negative for vessel growth.

Figure 4:
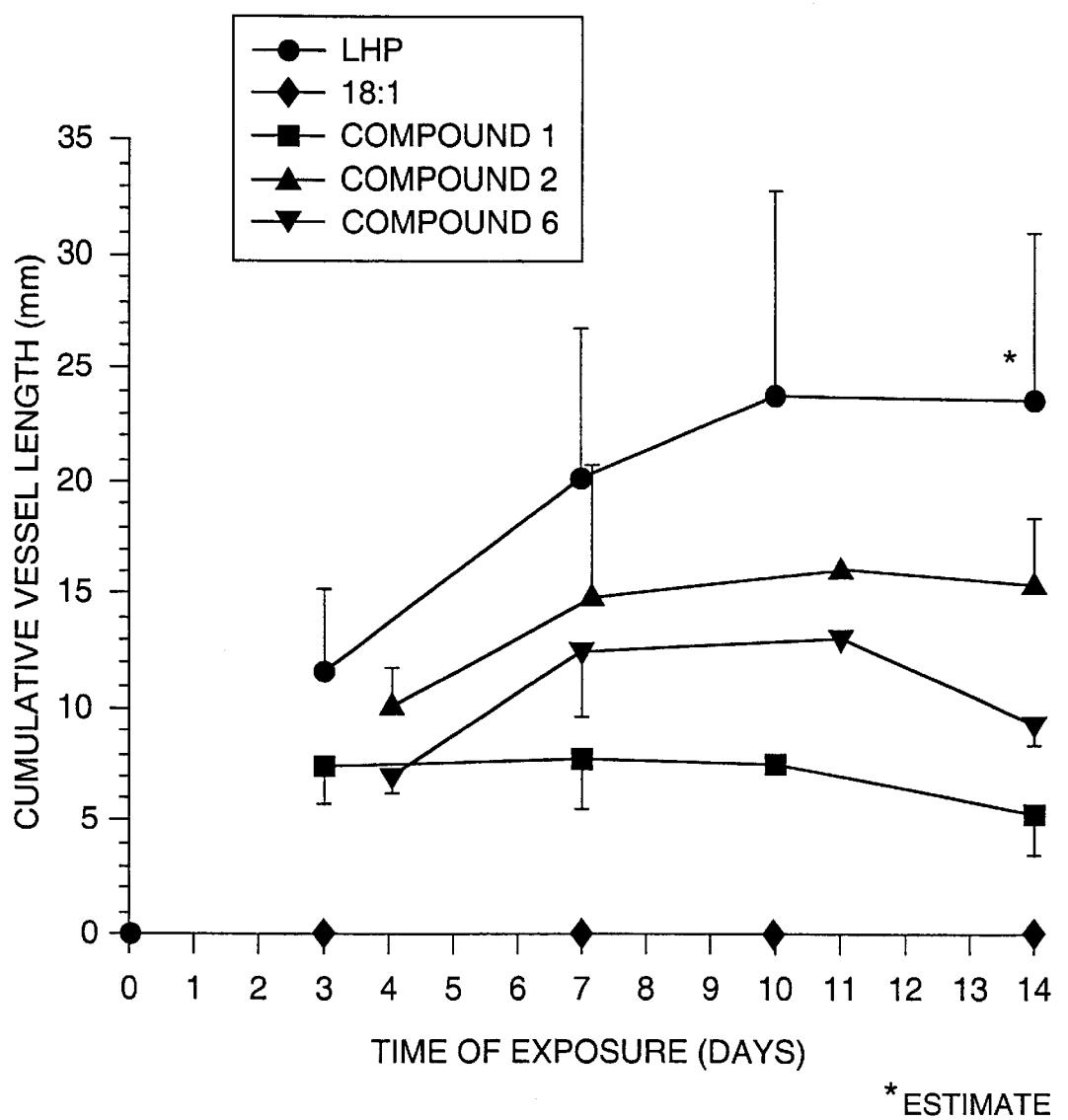
FIG. 4 is a graph illustrating the degree of corneal neovascularization observed in a lipid hydroperoxide-induced vascular growth experiment in the presence of compounds of the invention and in the absence of such compounds.

To quantitate the neovascular response, Kodachrome slides taken from each group of animals were projected onto a screen and the entire vascular bed traced with an Opsiometer. This provided a cumulative index of total vessel proliferation at the various time intervals. These results are shown in FIG. 4.

This study showed that Compound 1 was the most effective inhibitor of corneal neovascularization (38% at 3 days, 61% at 7 days, 67% at 10 days and 75–85% at 14 days post-exposure. Compound 6 was also effective; 42% at 4 days, 37% at 7 days 46% at 11 days and 58% at 14 days post-exposure. Compound 2 showed anti-neovascular properties, but was the least effective of the drugs tested (17% at 4 days, 27% at 7 days, 33% at 11 days and 37% at 14 days post-exposure).

From analysis of the slope and development of growth curves, it was determined that from 3 days until the end of the experiment, vessel proliferation was stopped completely by Compound 1. At 14 days, there was evidence for vessel retraction (from 7.5 mm to 6 mm). In contrast, vessels from Compound 6- and Compound 2-treated animals continued to grow in length and numbers until 10–11 days post-exposure. Compound 1 and Compound 6 showed the greatest amount of vessel retraction (20 and 23%, respectively).

Similar findings were obtained when the retina was examined. New vessels grew extensively in the LHP-treated animals without drug intervention. Numerous small branches were observed proximally and some were markedly dilated. At the distal end of vessels, there was extensive dilation and hemorrhage. In contrast, vessels in control animals injected with 18:1 showed no edema, neovascularization, or hemorrhage.

An animal treated with Compound 1 showed a reduction in neovascularization, but only slight effects on dilation and hemorrhage. Vasodilation edema and hemorrhage are prominent in an animal treated with Compound 2, however, no neovascularization was evident. Only dilation is observed in the retina treated with Compound 6.

As shown in Table 2, Compounds 1, 2 and 6 all greatly retarded the neovascularization process. The degree of retardation ranged from 87.5% for Compound 2, to 75% for Compound 6, to 62.5% for Compound 1.

EXAMPLE 4

An additional study was conducted. This study was based on the suggestion that certain cytokines play a role in the neovascularization process with the concentration of these cytokines being abnormal when the undesirable neovascularization takes place. An effective agent would correct these abnormalities. In one study, the concentration of the cytokine, vascular endothelial growth factor ("VEGF") was studied. VEGF concentration was measured by immunoassay (R&D Systems Quantkine kit). Measurements were made in control animals, control animals receiving an injection of LHP and test animals receiving LHP plus test compound. Measurements were carried out at the injection site and in the superior quadrant. LHP stimulated the maximum synthesis of VEGF between 6 to 24 hours.

TABLE 2

Retinal Data

| Rabbit # | CD or CS | Treatment | Dilation | Hemorrhage | Neovascularization | RD | Edema |
|---|---|---|---|---|---|---|---|
| 993 | CD | LHP - 14d | + | + | + | + | + |
|  | CS | LHP - 14d | + | + | + | – | – |
| 994 | CD | LHP - 14d | – | – | – | + | + |
|  | CS | LHP - 14d | + | + | + | + | + |
|  |  |  | 75% | 75% | 75% | 75% | 75% |
| 996 | CD | 18: 1 - 14d | – | – | – | – | – |
|  | CS | 18: 1 - 14d | – | – | – | – | – |
| 997 | CD | 18: 1 - 14d | – | – | – | – | – |
|  | CS | 18: 1 - 14d | – | – | – | – | – |
| 977 | CD | 1 - 7d | + | + | – | + | + |
|  | CS | 1 - 7d | + | + | + | + | – |
| 978 | CD | 1 - 7d | + | – | – | – | + |
|  | CS | 1 - 7d | + | – | – | – | – |
| 979 | CD | 1 - 14d | – | – | – | + | – |
|  | CS | 1 - 14d | – | – | – | – | – |
| 980 | CD | 1 - 14d | + | + | + | – | + |
|  | CS | 1 - 14d | + | + | + | – | – |
|  |  |  | 75% | 50% | 37.5% | 37.5% | 37.5% |
| 983 | CD | 2 - 7d | – | + | – | + | – |
|  | CS | 2 - 7d | + | + | – | + | – |
| 984 | CD | 2 - 7d | + | + | + | – | + |
|  | CS | 2 - 7d | + | – | – | – | + |
| 985 | CD | 2 - 14d | + | + | – | – | + |
|  | CS | 2 - 14d | + | + | – | – | – |
| 986 | CD | 2 - 14d | – | – | – | – | – |
|  | CS | 2 - 14d | – | + | – | – | + |
|  |  |  | 62.5% | 75% | 12.5% | 25% | 50% |
| 989 | CD | 6 - 7d | + | + | – | – | + |
|  | CS | 6 - 7d | + | – | + | – | – |
| 992 | CD | 6 - 7d | + | + | – | + | – |
|  | CS* | 6 - 7d | + | – | + | – | – |
| 990 | CD | 6 - 14d | – | – | – | – | – |
|  | CS | 6 - 14d | – | – | – | – | – |
| 991 | CD | 6 - 14d | + | – | – | – | – |
|  | CS | 6 - 14d | + | + | – | + | – |
|  |  |  | 75% | 37.5% | 25% | 25% | 12.5% |

*keratitis

Compounds 1, 2 and 6 showed differing effects on neovascular-associated phenomena in the retina. Vasodilation, hemorrhage, retinal detachment and edema were observed in 75% of the eyes injected with LHP. In contrast, the control vehicle (18:1 linoleic acid) evoked none of these responses in either right (OD) or left eyes (OS). Compounds 1, 2 and 6 were ineffective in controlling dilation or hemorrhage, although Compound 2 reduced the incidence to 37.5%. Retinal detachment was also reduced to a level of 25% by Compounds 2 and 6 and to a level of 37.5% by Compound 1). Retinal edema was reduced to 12.5% by Compound 6, to 37.5% by Compound 1 and to 50% by Compound 2.

a. Cornea

Figure 5:
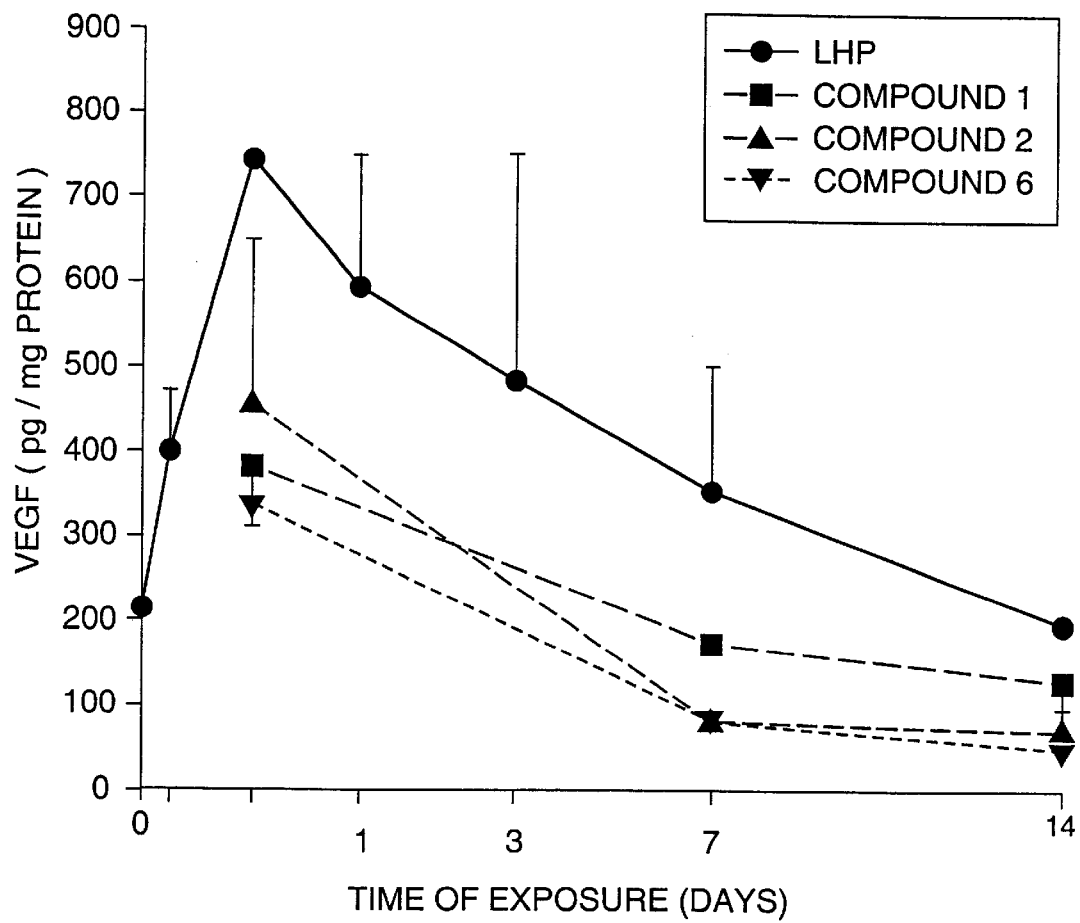
FIG. 5 is a graph of the concentration of VEGF in the cornea in the presence of lipid hydroperoxide with and without added NRT.

Since both areas (injection site and superior quadrant) were decreased in treated animals, the values were added together and averaged. The degree of reduction produced by NRT compounds at 12 hours post-injection of LHP ranged from 55% for Compound 6, to 48% for Compound 1 to 40% for Compound 2. The concentration of VEGF declined further to 50% to 75% levels at 7 days and 14 days. These results are presented graphically in FIG. 5.

b. Retina

Figure 6:
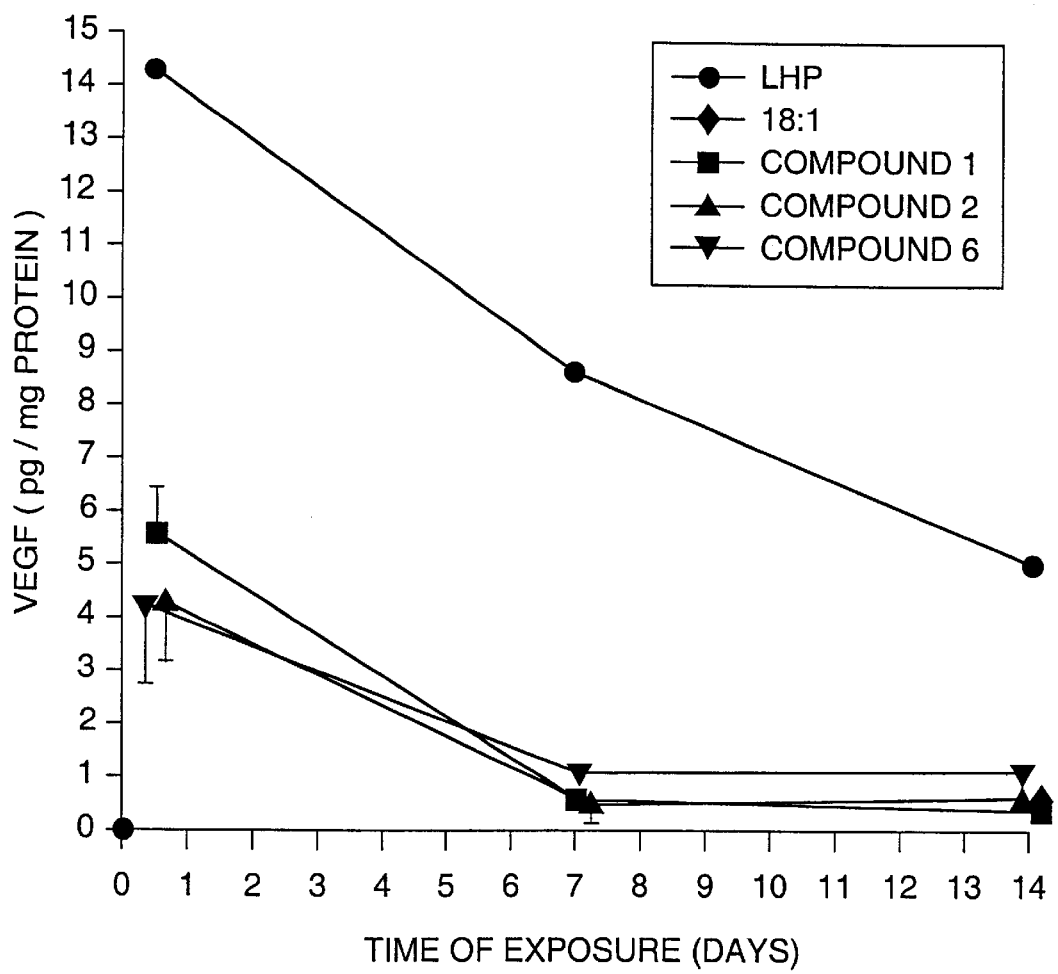
FIG. 6 is a graph of the concentration of VEGF in the retina in the presence of lipid hydroperoxide with and without added NRT.

VEGF was reduced by NRT compounds to a greater extent than observed in cornea. At 12 hours, 7 or 14 days, the difference was 30% greater in the retina (FIG. 6). By 14 days post-injection, Compound 1 inhibited VEGF production 92%, Compound 2 inhibited 86% and Compound 6 inhibited 76%. This placed all 3 drugs within the range of control samples. These results are presented graphically in FIG. 6.

c. Tumor necrosis factor alpha (TNFα) addition

Measurements of tumor necrosis factor alpha (TNFα) were added to the protocol to obtain a more comprehensive understanding of alterations occurring in the initiation of the angiogenic cytokine cascade. Tissue levels were quantified using a WEH1 cell bioassay which is specific for TNFα.

Figure 7:
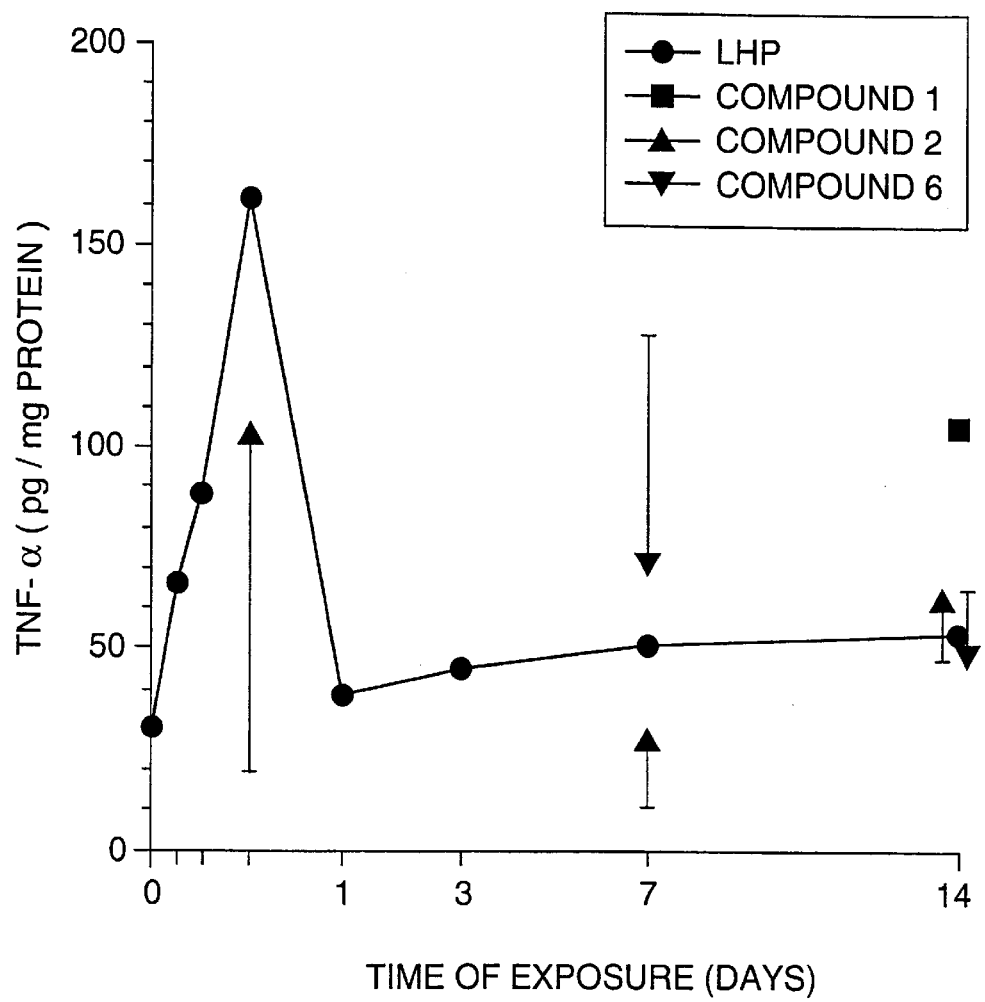
FIG. 7 is a graph of the concentration of tumor necrosis factor alpha in the cornea in the presence of lipid hydroperoxide with and without added NRT.

Previous studies in our laboratory have demonstrated that during the first day after LHP exposure, there is a dramatic increase in TNFα and if inhibitors (anti-TNFα or pentoxifylline) are added in vivo, neovascularization is markedly retarded. In the cornea, Compound 2 depressed TNFα levels at 12 hours by 36% and at 7 days was still 25% below LHP control levels. (These results are shown in FIG. 7) Corneal samples at 12 hours from Compound 1 and Compound 6 were contaminated. Compound 1- and Compound 6-treated rabbits had TNFα levels that were increased above the baseline at 7 and 14 days post-injection.

Figure 8:
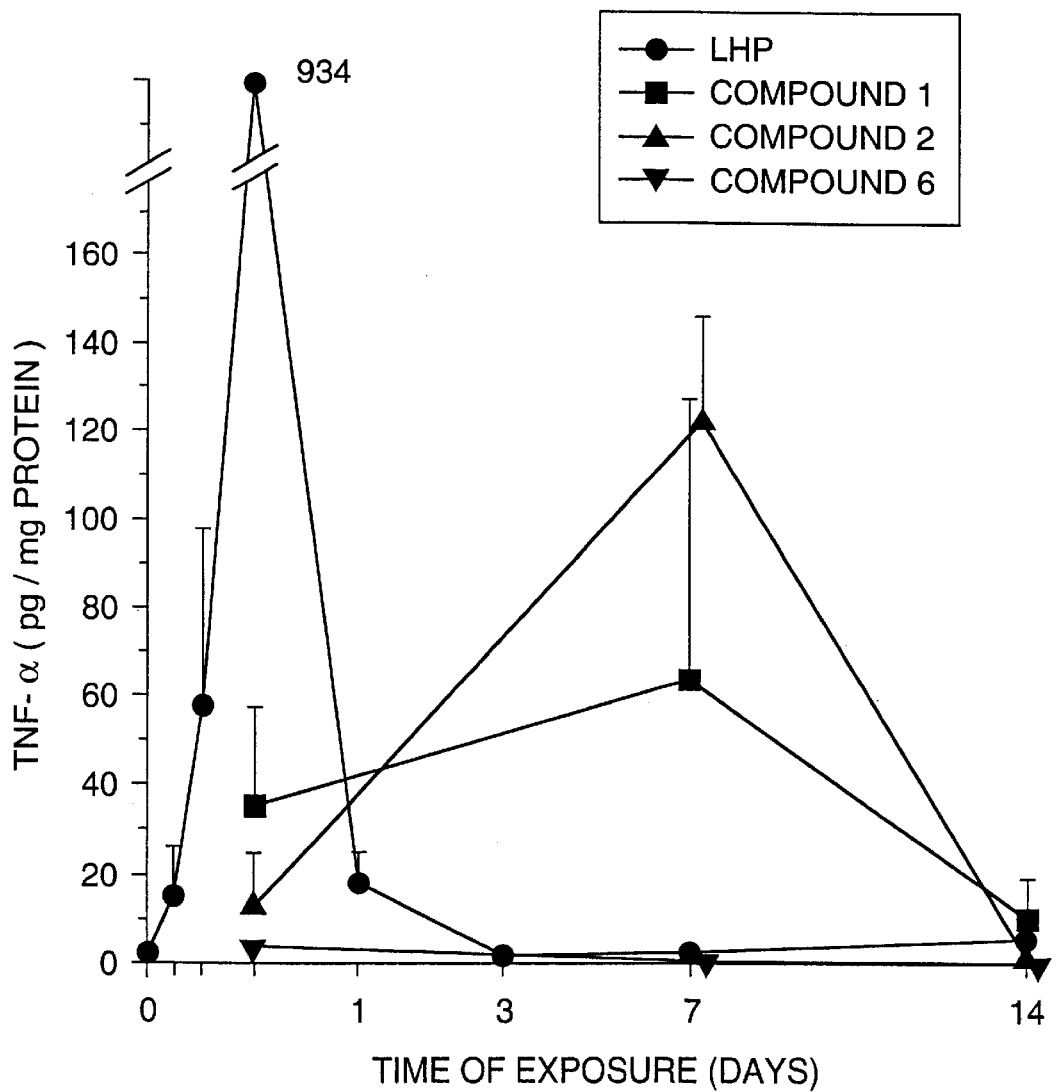
FIG. 8 is a graph of the concentration of tumor necrosis factor alpha in the retina in the presence of lipid hydroperoxide with and without added NRT.

In the retina, Compounds 1, 2 and 6 all inhibited TNFα synthesis, with Compound 6 showing the greatest effect at 12 hours post-injection. Compound 2 and Compound 1 appeared to stimulate new synthesis, at 7 days after exposure, and then dropped to low levels, whereas Compound 6 remained near baseline over the 14 days experimental period. (These results are presented in FIG. 8)

While early response of TNFα provides localized signals for synthesis of other cytokines to sustain growth and can be considered a pathological event, the increases at 7 days in retina and 14 days in cornea may represent secondary repair process. For example, TNFα may be cytotoxic in one situation and restorative in another. Therefore, repair stimuli may be regulated differently than the initial oxidative stress which initiated neovascularization from the parent vessel.

In summary, in this study all three NRT compounds tested showed an inhibitory effect on LHP induced neovascularization in both cornea and retina.

As a model for studying diabetic retinopathy, the effect of NRTs in protecting against induction and associated pathophysiologic changes by LHP was important. NRT compounds were observed to affect the synthesis of both TNFα and VEGF which are essential growth factors for the initiation and propagation of new vessels. The collective reduction of these cytokines would be expected to abate the neovascular responses. Retinal neovascular proliferation was reduced best (88%) by Compound 2 with the other two drugs ranging from 63% to 75%. Compound 6 appeared to be more effective against controlling edema, hemorrhage and retinal detachment. These results suggest the efficacy of using NRT compounds in the management of proliferative diabetic retinopathy.

Using a more easily visualized corneal model, a marked inhibitory effect was also observed. This, too, was correlated with statistically significant reductions in the cytokine growth factors TNFα and VEGF.

What is claimed is:

1. A method for inhibiting angiogenesis in a patient susceptible thereto comprising
    administering to said patient an effective angiogenesis-inhibiting dose of a pharmaceutical composition having a nitrone-related therapeutic as an active ingredient.
2. The method of claim 1 wherein the administering is systemically administering.
3. The method of claim 2 wherein the systemically administering is orally systemically administering.
4. The method of claim 2 wherein the systemically administering is parenterally systemically administering.
5. The method of claim 1 wherein the administering is locally administering.
6. The method of claim 5 wherein the locally administering is intraocularly administering.
7. The method of claim 5 wherein the pharmaceutical composition is an eye ointment composition, eye drop solution or eye drop suspension composition which is topically instilled into the eye of the patient.
8. The method of claim 1 wherein the angiogenesis is angiogenesis associated with solid tumor.
9. The method of claim 8 wherein the administering is systemically administering.
10. The method of claim 8 wherein the administering is locally administering.
11. The method of claim 10 wherein the locally administering is administering by close intra-arterial delivery to a site associated with the angiogenesis.
12. The method of claim 1 wherein the angiogenesis is angiogenesis associated with psoriasis.
13. The method of claim 1 wherein the angiogenesis is angiogenesis associated with rheumatoid arthritis.
14. The method of claim 1 wherein the nitrone related therapeutic is an aromatic nitrone.
15. The method of claim 14 wherein the aromatic nitrone is selected from the group consisting of PBN, a PBN analog, DMPO, a DMPO analog POBN and a POBN analog.
16. The method of claim 1 wherein the aromatic nitrone is selected from the group consisting of
    3,5-dimethyl-4-hydroxyphenyl-N-n hexyl nitrone;
    3,5-dimethoxy-4-hydroxyphenyl-N-t butyl nitrone;
    2,4-disulfophenyl-N-ethyl nitrone, sodium salt;
    2,4-disulfophenyl-N-isopropyl nitrone, sodium salt;
    2,4-dihydroxyphenyl-N-t butyl nitrone;
    2,4-disulfophenyl-N-n butyl nitrone, sodium salt;
    2,4-disulfophenyl-N-1,1-dimethyl-2-hydroxyethyl nitrone, sodium salt; and
    2,4-disulfophenyl-N-t amyl nitrone, sodium salt.
17. The method of claim 1 wherein the aromatic nitrone is 3,5-dimethyl-4-hydroxyphenyl-N-n hexyl nitrone.
18. The method of claim 1 wherein the aromatic nitrone is 3,5-dimethoxy-4-hydroxyphenyl-N-t butyl nitrone.
19. The method of claim 1 wherein the aromatic nitrone is 2,4-dihydroxyphenyl-N-t butyl nitrone.
20. The method of claim 1 wherein the administering is therapeutically administering.
21. The method of claim 1 wherein the administering is prophylactically administering.
22. A pharmaceutical composition for use in the treatment of angiogenesis comprising an effective angiogenesis-treating concentration of a nitrone-related therapeutic selected from the group consisting of
    3,5-dimethyl-4-hydroxyphenyl-N-n hexyl nitrone;
    2,4-disulfophenyl-N-ethyl nitrone, sodium salt;
    2,4-disulfophenyl-N-isopropyl nitrone, sodium salt;
    2,4-dihydroxyphenyl-N-t butyl nitrone;
    2,4-disulfophenyl-N-n butyl nitrone, sodium salt;
    2,4-disulfophenyl-N-1,1-dimethyl-2-hydroxyethyl nitrone, sodium salt; and
    2,4-disulfophenyl-N-t amyl nitrone, sodium salt in a pharmaceutically acceptable carrier.
23. A nitrone-related therapeutic compound selected from the group consisting of 3,5-dimethyl-4-hydroxyphenyl-N-n hexyl nitrone;
2,4-disulfophenyl-N-ethyl nitrone, sodium salt;
2,4-dihydroxyphenyl-N-t butyl nitrone;
2,4-disulfophenyl-N-n butyl nitrone, sodium salt;
2,4-disulfophenyl-N-1,1-dimethyl-2-hydroxyethyl nitrone, sodium salt; and 2,4-disulfophenyl-N-t amyl nitrone, sodium salt.

24. The nitrone-related therapeutic compound of claim 23 being 3,5-dimethyl-4-hydroxyphenyl-N-n hexyl nitrone.

25. The nitrone-related therapeutic compound of claim 23 being 2,4-dihydroxyphenyl-N-t butyl nitrone.

* * * * *